United States Patent [19]

Nash

[11] 4,099,884
[45] Jul. 11, 1978

[54] OPTICAL INSPECTION SYSTEMS

[76] Inventor: Paul Nash, Kinfauns, Worthing Rd., Horsham, Sussex, England

[21] Appl. No.: 708,049

[22] Filed: Jul. 23, 1976

[30] Foreign Application Priority Data

Jul. 25, 1975 [GB] United Kingdom ............... 31221/75

[51] Int. Cl.² ............................................. G01N 21/32
[52] U.S. Cl. ..................................... 356/200; 250/572
[58] Field of Search ............... 250/559, 562, 571, 572; 356/199, 200

[56] References Cited

U.S. PATENT DOCUMENTS

| 3,105,152 | 9/1963 | Nash | 356/200 |
|---|---|---|---|
| 3,666,370 | 5/1972 | Seaholtz | 356/200 |
| 3,827,809 | 8/1974 | Nash | 356/200 |
| 3,841,761 | 10/1974 | Selgin | 250/562 |

FOREIGN PATENT DOCUMENTS

| 1,412,868 | 8/1965 | France | 250/562 |

Primary Examiner—John K. Corbin
Assistant Examiner—R. A. Rosenberger
Attorney, Agent, or Firm—Browdy & Neimark

[57] ABSTRACT

A non-contacting optical inspection system for detecting blemishes in sheet material, of the kind in which light directed onto the sheet as it flows past an inspection head is reflected onto photosensitive detectors, is provided with means for varying the relative sensitivities of the system to optical defects, such as spots, and mechanical defects, such as lumps or creases, so that the system can be adjusted to be equally sensitive to both types of defect. The inspection head containing lamp, photosensitive detectors and a collimating system including apertures through which reflected light is transmitted to the detectors, is so mounted that it can be raised and lowered and also rotated about a horizontal axis to enable the angle of incidence of light on the sheet material to be varied while maintaining the distance of the aperture from the sheet substantially constant.

10 Claims, 3 Drawing Figures

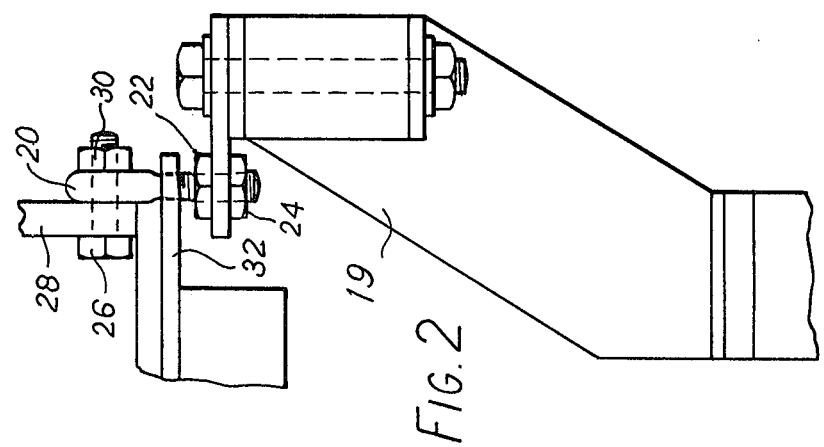
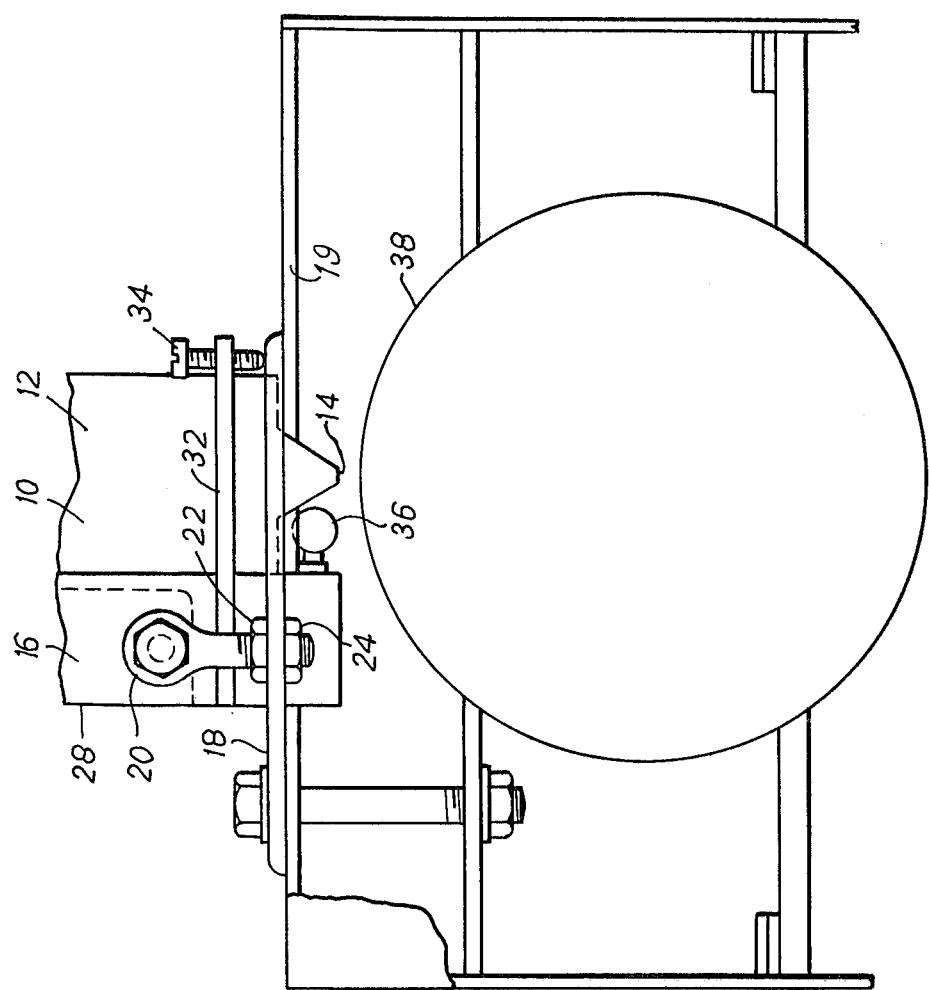

OPTICAL INSPECTION SYSTEMS

FIELD OF THE INVENTION

This invention relates to apparatus for detecting blemishes in sheet material.

More particularly, the invention relates to apparatus for detecting blemishes in sheet material arranged to flow past an inspection head of the apparatus, of the kind comprising light source means arranged to direct light into the sheet material and photosensitive means in the inspection head arranged to receive light reflected from or transmitted through the sheet material as it passes the inspection head. An example of such apparatus is that described in U.S. Pat. No. 3,827,809.

BACKGROUND OF THE INVENTION

When considering the inspection of sheet materials such as paper, plastics or textiles it is desirable to differentiate between mechanical and optical defects. Mechanical defects are creases, lumps, that is elevation type defects which are not associated with discolorations. Such defects cannot be seen when the sheet is illuminated by omnidirectional light, or by a light source which is in line with the eye of the observer. Optical defects are for example spots, holes, or faint disclorations, that is defects which can be seen when illuminated from any angle.

On some type of materials, such as medium grade papers for printing, optical defects when small are of minor significance, whereas creases, lumps and tears are far more important for the printer because such defects can interfere with the printing and can spoil the printing blanket.

Mechanical defects can be made visible with the aid of shallow illumination which gives rise to shadows. The shallower the illumination the greater is the area of shadow produced by a given defect. Hence the optical system of the detection apparatus can detect the slightest mechanical defect if the mean angle of incidence of the illumination can be made shallow enough and the intensity of illumination high enough.

In order to obtain as high a light intensity as possible on the section of the sheet material which is observed through the aperture of a collimating optical system the lamp is placed as close as possible to the aperture and the sheet. If one now tries to reduce the angle of incidence of the illumination and at the same time maintain the distance between the aperture and the sheet one finds that this is only possible by either exposing the lamp so that it can be moved nearer the sheet, with danger of breakage of the lamp, or by moving the lamp farther away from the observed section of the sheet. As the intensity of the illumination of the sheet is inversely proportional to the square of the distance of the lamp from the inspected sheet section the latter method for achieving shallower illumination is not practical. Also it is difficult to provide sufficient space for the lamp movement as the inspection system has to be as compact as possible.

SUMMARY OF THE INVENTION

According to this invention there is provided apparatus of the kind set forth, in which there are provided means for varying the relative sensitivities of the apparatus to mechanical and optical defects.

Preferably the light source means are arranged on the same side of the path of sheet material as the photosensitive means, the photosensitive means being arranged to receive light reflected from sheet material as it passes the inspection head, and means are provided for varying the mean angle of incidence of light falling onto the area of sheet material from which light is reflected to the photosensitive means.

Advantageously, there is provided a cylindrical roller over which sheet material is trained as it passes the inspection head, the head includes a collimating system by means of which the photosensitive means receives only light reflected from a narrow strip-like area of the surface of the sheet material extending parallel to the axis of the roller, and the means for adjusting the angle of incidence of the light includes means for adjusting the collimating system so as to displace circumferentially relative to the light source means the area of the surface from which light is received by the photosensitive means.

BRIEF DESCRIPTION OF THE DRAWINGS

The invention will now be described, by way of example, with reference to the accompanying diagrammatic drawings, in which:

FIG. 1 is a side elevation of apparatus constructed in accordance with the invention, FIG. 2 is a fragmentary front elevation of the apparatus of FIG. 1.

DESCRIPTION OF PREFERRED EMBODIMENTS

Figure 3:
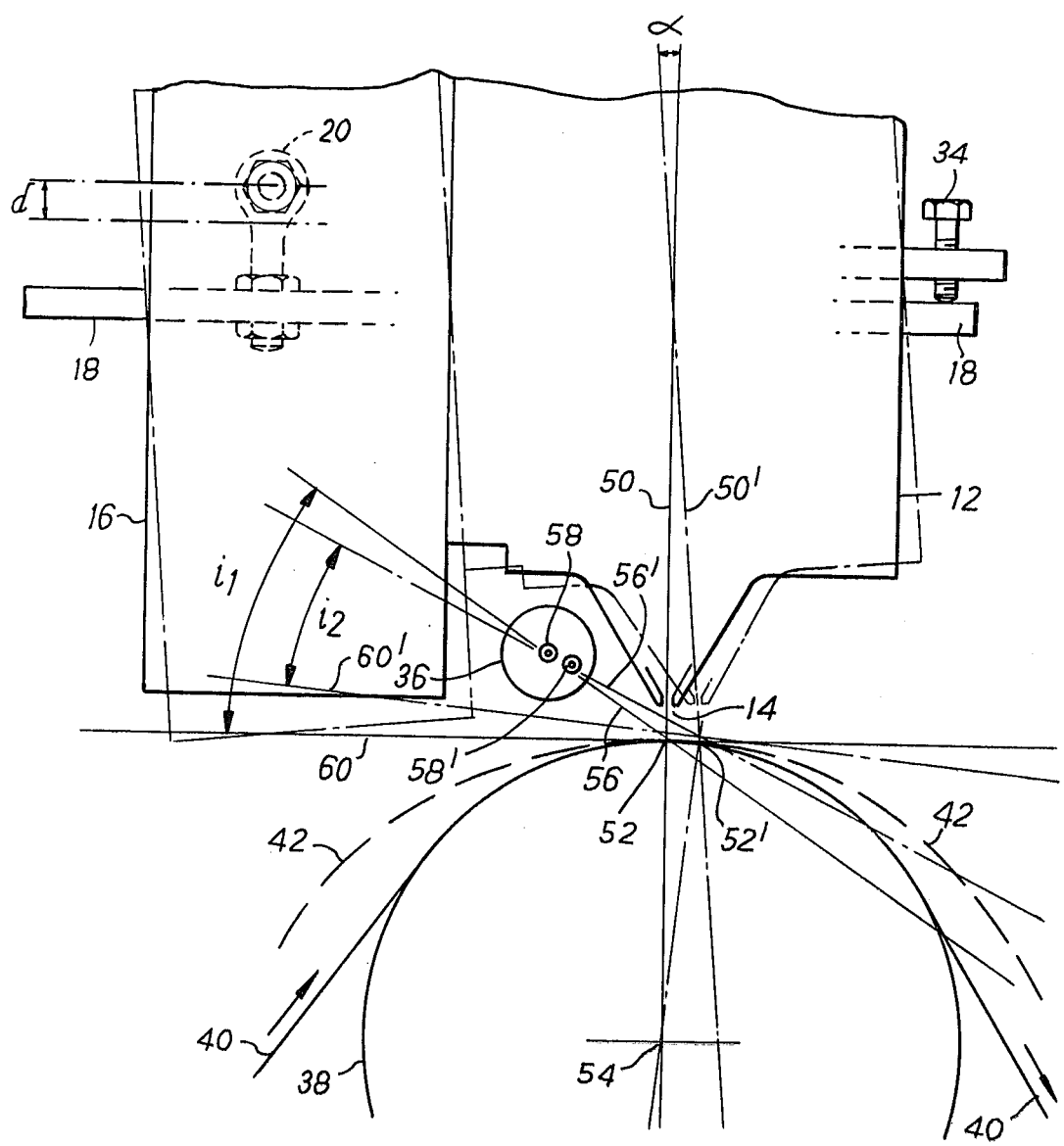
FIG. 3 is a side elevation showing diagrammatically the geometry of the optical system of the apparatus in two positions of the inspected head.

Referring to the drawings, the apparatus comprises an inspection head 10 consisting of a series of unit head sections 12, as described in U.S. Pat. No. 3,827,809. Each head section contains a series of photosensitive detectors and a collimating optical system having an aperture 14. The head sections 12 are fixed to a beam 16 consisting of rectangular section tubing which can be air pressurized as described in U.S. Pat. No. 3,827,809. An illuminating lamp 36, for example a neon fluorescent tube, is mounted in suitable holders beneath the head sections 12.

The beam 16 is adjustably mounted on two support plates 18, one at each end of the inspection head, which are bolted to the main frame 19 of the apparatus. The beam 16 is connected to each support plate 18 by means of a rod-end bearing 20 the threaded shank of which passes freely through a hole in the associated plate 18 and is secured by two nuts 22 and 24. A bolt 26 passes through the eye of the rod-end bearing 20 and a hole in an end plate 28 of the beam 16 and is secured by a nut 30 so as to allow the head 10 to be rotated about the axis defined by the rod-end bearings, between an operative positions and a raised position which allows access to the apertures 14 and lamp 36. By adjusting the nuts 22 and 24, each rod-end bearing can be raised or lowered.

At each end of the inspection head a plate 32 fixed to the beam 16 extends alongside the end of the adjacent head section 12. An adjusting screw 34 passes through a threaded bore in each plate 32 and engages the upper face of the adjacent support plate 18. Adjustment of the screws 34 in conjunction with the raising and lowering of rod-end bearings 20, enables the inspection head 10 to be rotated about an axis parallel to that of the rod-end bearings whilst the distance of the apertures 14 from the sheet to be inspected is maintained substantially constant, as described below.

Mounted in the main frame 19 of the apparatus beneath the inspection head 10 is a roller 38 over which passes the sheet material 40 to be inspected, as shown in FIG. 3.

FIG. 3 shows diagrammatically the geometry of the system, with the inspection head 10 in one position shown in solid lines and a second position shown in broken lines after adjustment of the rod-end bearings 20 and adjusting screws 34.

The line 50 represents the plane passing through the photosensitive detectors of the inspection head and the apertures 14 of the collimating systems. The inspection head "sees" only a narrow line 52, termed the inspect line, at the surface of the sheet 40. The inspect line 52 is defined by the intersection of plane 50 with the sheet 40 and is at right angles to the direction of sheet movement past the inspection head. In the solid line position of the inspection head the plane 50 passes also through the axis 54 of roller 38. Line 56 represents the mean light beam from lamp 36, defined by the plane containing the inspect line 52 and the axis 58 of lamp 36. The angle of incidence $i_1$ of the light on the sheet 40 at the inspect line 52 is the angle between line 56 and the line 60 defined by the plane tangential to the surface of roller 38 at the inspect line. In the solid line position of the inspection head, line 60 is at right angles to the line 50 defined by the head unit collimating systems.

On lowering each of the rod-end bearings 20 through a distance $d$ and adjusting screws 34 to cause the inspection head to rotate through an angle whilst the distance of the collimating apertures 14 from the sheet 40 remains unchanged, the line 50 defined by the head unit collimating systems moves to the position shown at 50', so that the inspect line is displaced to the position 52'. As a result, the mean angle of incidence of the light on the sheet at the inspect line is changed to $i_2$, defined by the angle between the plane 60' tangential to the roller at the new inspect line 52' and the plane 56' containing the new inspect line 52' and the axis 58' of the displaced lamp 36.

It will be seen that the angle of incidence of the light is reduced considerably for a relatively small movement of the inspection head, owing to the rotational displacement of both the plane 56 to 56' and of the tangential plane 60 to 60'. It has been found for example that with the apparatus of the described embodiment, employing a 4 inch (10.2 cm) diameter inspection roller, a lowering of the rod-end bearings by 5 millimeter and rotation of the head by 4° results in a change of the mean angle of incidence from 32° to 20°.

In adjusting the head position, the lowering of the rod-end bearings 20 and adjustment of the screws 34 must be carried out in such a manner that the distance of the collimating apertures 14 from the inspect line is maintained substantially constant. In the described embodiment it has been found in practice that a linear relationship between the two adjustments, i.e., with the screws 34 being "screwed in" 1 millimeter to raise the corresponding side of the head 1 millimeter for every millimeter that the rod-end bearings 20 are lowered, ensures that the distance of the apertures from the inspect line remains closely enough constant, though it does not remain precisely constant owing to the displacement of the inspect line. This arrangement is practicable since the distance of the apertures 14 from the sheet is not critical.

In operation, the sensitivity of the apparatus to optical and mechanical defects may be adjusted using a sheet 40 containing known defects corresponding to the required limits of sensitivity. The limits might for example be, for optical defects, a 1 millimeter square full black spot and, for mechanical defects, a crease which is 0.05 millimeter high and ½ inch (13 mm) long and which extends at an angle of 30° to the direction of sheet travel. Initially, the inspection head is placed in an operative position, with the rod-end bearings 20 and screws 34 adjusted to give an optimum distance between the apertures 14 and the roller 38. The sheet with the known defects is then passed over the roller 38, and the sensitivity of the apparatus to optical defects is adjusted, by adjusting the gain control of the amplifiers which receive the signals from the photosensitive detectors, as in the apparatus of U.S. Pat. No. 3,827,809, to give the required output signal amplitude. If the signal level for the crease is found to be lower than that for the spot, the rod-end bearings 20 are lowered and screws 34 adjusted to rotate the inspection head 10 anticlockwise as seen in FIG. 3. It will be found that the signal levels for both spot and crease have been reduced, and the gain of the amplifier is therefore adjusted to bring the signal level for the spot back to its required value. This will increase the signal level for the crease by more than that for the spot, owing to the effect of the decreased angle of incidence of light on the sheet 40, so that the signal level for the crease will have been brought nearer to equality with that for the spot. The adjustments are repeated until the signal levels for the crease and spot are both at the same, required level.

It will be seen from FIG. 3 that the angle of incidence of light onto the sheet 40 at the inspect line could be decreased by simply lowering the lamp 36. This method is however unsafe because of the risk of damage to the fragile glass envelope of the lamp if it protrudes beyond the nose casting of apertures 14. Moreover, lowering of the lamp is often impossible where, because of the heavy caliper of the sheet to be inspected, the inspection roller 38 has to have a larger diameter of say, 8 or 12 inches, e.g., as indicated in broken lines at 42 in FIG. 3.

It will be appreciated that modifications could be made in the described embodiment. For example, other mechanisms could be used to provide the necessary adjustability of the position of the inspection head.

I claim:

1. Apparatus for detecting blemishes in sheet material arranged to flow past an inspection head of the apparatus, comprising light source means arranged to direct light onto the sheet material and photosensitive means in the inspection head arranged to receive light reflected from or transmitted through the sheet material as it passes the inspection head, in which means are provided for adjusting the relative sensitivity of the apparatus to mechanical and optical defects, in which the light source means are arranged on the same side of the path of sheet material as the photosensitive means, the photosensitive means being arranged to receive light reflected from sheet material as it passes the inspection head, and means are provided for varying the mean angle of incidence of light falling onto the area of sheet material from which light is reflected to the photosensitive means, in which there is provided a cylindrical roller over which sheet material is trained as it passes the inspection head, the head includes a collimating system by means of which the photosensitive means receives only light reflected from a narrow strip-like area of the surface of the sheet material extending parallel to the axis of the roller, and the means for adjusting the angle of incidence of the light includes means for adjusting the collimating system so as to displace circumferentially relative to the light source means the area of the surface from which light is received by the photosensitive means.

2. Apparatus as claimed in claim 1, in which the light source means and collimating system are mounted in the inspection head, and the means for adjusting the angle of incidence of the light comprises means for rotating the inspection head about an axis parallel to that of the roller and for effecting translation movement of head in a direction towards and away from the axis of the roller.

3. Apparatus as claimed in claim 2, in which the inspection head is supported on a main frame of the apparatus by two rod-end bearings arranged one at each end of the head, the bearings allowing rotation of the head about an axis defined by the bearings and being movable relative to the main frame in the said direction.

4. Apparatus as claimed in claim 3, in which adjustment of the angular position of the head about the axis defined by the rod-end bearings is effected by means of adjusting screws acting between the inspection head and the main frame in a plane spaced from the said axis.

5. Apparatus for detecting blemishes in sheet material comprising an inspection head, guide means for guiding sheet material to flow past the inspection head, light source means arranged to direct light onto the sheet material and photosensitive means in the inspection head arranged to receive light reflected from the sheet material, and adjustment means for mechanically adjusting the position of the inspection head relative to the sheet material to vary the mean angle of incidence of light falling onto the area of sheet material from which light is reflected to the photosensitive means whilst maintaining substantially constant the distance between said area of sheet material and said photosensitive means, thereby to vary the sensitivity of the apparatus to mechanical defects relative to the sensitivity of the apparatus to optical defects.

6. Apparatus as claimed in claim 5, in which the guide means comprises a curved member in the form of a roller.

7. Apparatus for detecting blemishes in sheet material comprising an inspection head, guide means for guiding sheet material to flow past the insepction head, light source means arranged to direct light onto the sheet material and photosensitive means in the inspection head arranged to receive light reflected from the sheet material, and adjustment means for mechanically adjusting the position of the inspection head relative to the sheet material to vary the sensitivity of the apparatus to mechanical defects relative to the sensitivity of the apparatus to optical defects, in which the light source means are arranged in the inspection head on the same side of the path of sheet material as the photosensitive means, the photosensitive means being arranged to receive light reflected from sheet material, and the adjustment means are adapted to vary the mean angle of incidence of light falling onto the area of sheet material from which light is reflected to the photosensitive means, and wherein the guide means includes a convex curved member over which sheet material is trained as it passes the inspection head, the head includes a collimating system by means of which the photosensitive means receives only light reflected from a narrow strip-like area of the surface of the sheet material extending parallel to the axis of the curved member, and the adjustment means includes means for adjusting the collimating system so as to displace circumferentially relative to the light source means the area of the surface from which light is received by the photosensitive means, thereby to vary the mean angle of incidence of light falling onto the strip-like area.

8. Apparatus as claimed in claim 7, in which the light source means and collimating system are mounted in the inspection head, and the adjustment means comprises means for rotating the inspection head about an axis parallel to that of the curved member and for effecting translation movement of the head in a direction towards and away from the axis of the curved member.

9. Apparatus as claimed in claim 8, in which the inspection head is supported on a main frame of the apparatus by two rod-end bearings arranged one at each end of the head, the bearings allowing rotation of the head about an axis defined by the bearings and being movable relative to the main frame in the said direction.

10. Apparatus as claimed in claim 9, in which adjustment of the angular position of the head about the axis defined by the rod-end bearings is effected by means of adjusting screws acting between the inspection head and the main frame in a plane spaced from the said axis.

* * * * *